United States Patent [19]
Lahille et al.

[11] Patent Number: 5,743,912
[45] Date of Patent: Apr. 28, 1998

[54] UPPER FEMORAL EPIPHYSIS OSTEOSYNTHESIS IMPLANT

[75] Inventors: Michel Lahille, Vauhallan; Philippe Cottin, Saint Remy Les Chevreuse; Christian Maresca, Marseilles, all of France; Toshio Yamaguchi, Kobe, Japan

[73] Assignee: Biomat, Saclay, France

[21] Appl. No.: 696,519

[22] Filed: Aug. 14, 1996

[30] Foreign Application Priority Data

Aug. 23, 1995 [FR] France ............... 95 10076

[51] Int. Cl.⁶ .................................... A61B 17/76
[52] U.S. Cl. ....................... 606/65; 606/69; 606/73
[58] Field of Search ............... 606/65, 66, 62, 606/63, 64, 67, 68, 72, 73, 69, 70, 71, 61, 60

[56] References Cited

U.S. PATENT DOCUMENTS

3,051,169  8/1962  Grath ............................ 606/65
5,531,748  7/1996  De La Caffiniere ............ 606/62
5,580,352  12/1996  Sekel ............................ 623/23
5,665,087  9/1997  Huebner ........................ 606/65

*Primary Examiner*—Guy V. Tucker
*Attorney, Agent, or Firm*—Laubscher & Laubscher

[57] ABSTRACT

A longitudinal revascularization conduit is formed in the body of an implant. It is blind at the distal end of the body to be implanted in one bone fragment, such as the trochanter, and open via transverse orifices and at the proximal end of the body to be implanted in another bone fragment, such as the femoral head. At least one self-tapping section situated at the distal end of the body immobilizes the body in the bone, or an anchor end-piece is slidably mounted on the body and contains a damping device adapted to push the end-piece in the proximal direction and the body in the distal direction in order to maintain the fracture in compression. The distal end of the body may be mounted in a cylindrical portion of a plate secured on the diaphysis of the femur.

12 Claims, 6 Drawing Sheets

UPPER FEMORAL EPIPHYSIS OSTEOSYNTHESIS IMPLANT

BACKGROUND OF THE INVENTION

1—Field of the Invention

The present invention concerns an implant in particular for upper femoral epiphysis osteosynthesis to hold together bone fragments separated by a localized fracture in the neck of the femur or under the head of the femur.

2—Description of the Prior Art

An osteosynthesis implant of this kind is in the form of an osteosynthesis metal plate, also known as a nail-plate or screw-plate, having a short upper branch and a long lower branch separated by an elbow. The plate mates substantially with the vertical profile of the external face of the femur between the upper epiphysis and the femoral diaphysis so that it can be fixed to this face. One or two long parallel self-tapping screws pass through the trochanter and the neck of the fractured femur and are screwed into the head of the femur. The usually countersunk head of this screw is buried in a countersink in the short upper branch of the plate applied to the external face of the epiphysis. Between three and eight shorter screws are screwed perpendicularly into the femoral diaphysis to hold the long lower branch of the plate against the external face of the diaphysis.

The fixing of the long branch of the plate to the diaphysis holds immobile the short branch on which a long screw bears in order to unite the femoral head fragment against the trochanter fragment.

The long solid screws cause an imbalance in the intracephalic pressure in the bone fragments at the center of the site of the necrosis where vascular irrigation has been eliminated as a result of the fracture. Further, the length of the plate and the large number of screws require a large operation field and a long operation.

OBJECT OF THE INVENTION

The main object of this invention is to provide an implant of long screw type enabling revascularization of a fragmented bone focus.

SUMMARY OF THE INVENTION

An implant for osteosynthesis of a fracture between a first bone fragment and a second bone fragment comprises an elongate rectilinear body having a self-tapping portion at a proximal end of the body to be implanted in the first bone fragment or at a distal end of the body to be implanted in the second bone fragment. Transverse orifices are provided in the body through which there opens a longitudinal conduit having a blind distal end and an open proximal end.

Although the implant of the invention can be used to join at least two bone fragments on either side of a fracture located in particular at the level of the bony epiphysis, it is intended in particular for osteosynthesis of an upper femoral epiphysis which is the location of a fracture at the level of the femoral neck or under the femoral epiphysis head. In this latter case, the first bone fragment is part of the femoral head and the second bone fragment is part of the femoral trochanter.

According to a first embodiment, the longitudinal revascularization conduit is obstructed by a plug located at the distal end of the implant body. This plug is intended for preventing any extravasation from the longitudinal conduit to the external face of the epiphysis. The plug can be screwed in the distal end of the conduit; particularly, the distal end of the conduit comprises a screwthread into which a screwthreaded shank of the plug is screwed.

For screwing the body into a bored hole in the bone fragments, the distal end of the conduit comprises a counterbore opening to the exterior of the body and having a preferably polygonal cross-section to receive a complementary cross-section end of a key for screwing the body into the previously bored hole in the first and second bone fragments.

According to the first embodiment, the self-tapping portion is located at the distal end of the body whereby the body anchors in the second bone fragment, such as the trochanter. Preferably, the self-tapping portion comprises two screwthreaded sections having different screwthreads so as to immobilize in translation the body in the second bone fragment after bone forms around the body of the implant. The difference in the screwthreads between the two screwthreaded sections may be a difference between their pitches and/or may be a difference between their diameters.

According to an example of prefered embodiment, the self-tapping portion comprises a proximal screwthreaded section and a distal screwthreaded section having a pitch and/or a nominal diameter respectively greater than the pitch and/or the nominal diameter of the proximal screwthreaded section.

According to a second embodiment, the self-tapping portion is located at the proximal end of the body to be installed in the first bone fragment, such as femoral head. This self-tapping portion, as also in the first embodiment, can comprise at its distal end at least one longitudinal notch for starting screwthread cutting.

In the second embodiment, means are provided for compressing the fracture, i.e., for pressing the bone fragments together to obtain an assembly of maximal solidity without using any form of seating, such as an osteosynthesis plate, on the external face of the diaphysis. To achieve this compression, at the distal end of the body is provided an end-piece slidably mounted on an intermediate portion of the body and containing a damping means adapted to push the end-piece in the proximal direction and the body in the distal direction. In this way, the self-tapping portion anchored in the first bone fragment such as the femoral head is drawn towards the fracture and therefore towards the second bone fragment, such as the trochanter, and the end anchored in the second bone fragment is pushed in the opposite direction, also towards the fracture.

The damping means is preferably a coil spring which can be covered with a synthetic plastic material thereby slowing its expansion after implantation. The coil spring is housed in the end-piece so that a proximal end of the coil is pressed against an internal shoulder in the end-piece, and a member linked to the distal end of the body is placed against the distal end of the coil. This member can be a screwthreaded plug which is screwed onto a screwthreaded section at the distal end of the body and which is housed in a conduit internal to the end-piece.

More precisely, the end-piece can comprise an internal conduit including at least a proximal counterbore and an intermediate counterbore in the distal direction. The proximal counterbore can have a polygonal cross-section to slide on a polygonal cross-section intermediate portion of the body that can be substantially situated at the distal end of the longitudinal conduit in the body. The intermediate counterbore is preferably wider than the proximal counterbore to receive the damping means, such the above mentioned coil, pressed against a shoulder between the proximal and intermediate counterbores. A member housed in the end-piece is linked to the distal end of the body to press the damping means against the shoulder.

To screw together the body and the end-piece respectively into the first and second bone fragments, in particular into the femoral head and the femoral trochanter, the internal conduit in the end-piece includes a distal counterbore, that may be wider than the intermediate counterbore, having a preferably polygonal cross-section to receive a complementary key for screwing the body and the end-piece respectively into the first and second bone fragments.

In an analogous manner to the self-tapping portion located at the distal end of the body in the first embodiment, the periphery of the end-piece according to the second embodiment may comprise a first self-tapping section. The pitch of the first self-tapping section is preferably substantially equal to that of the proximal self-tapping section of the body thereby facilitating the screwing both the end-piece and the proximal self-tapping portion of the body.

The periphery of the end-piece may comprise a second self-tapping section having a screwthread different from that of the first self-tapping section, if provided, and/or different from that of the self-tapping portion at the proximal end of the body, i.e., having a pitch and/or a diameter different from the respective ones of said self-tapping portion. This feature prevents any unscrewing of the end-piece and movement of the end-piece in the distal direction. According to an example, the periphery of the end-piece comprises at its proximal end the first self-tapping section and at its distal end the second self-tapping section that has a pitch and/or a nominal diameter respectively greater than the pitch and the nominal diameter of the first self-tapping section.

According to a third embodiment intended to consolidate sub-trochanter fractures, the implant further comprises a plate having an anchor portion adapted to be fixed against the diaphysis of the second bone fragment and a cylindrical portion through which the end-piece slides and against which a distal base of the end-piece is pressed. The cylindrical portion of the plate is oblique to the anchor portion of the plate whereby the body is held substantially perpendicular to the fracture.

The implant may comprise a means disposed between the distal base of the end-piece and the cylindrical portion of the plate for damping relative displacements between the end-piece and the plate.

The damping means comprises a damper material washer that is preferably in contact with one or two metal washers.

Preferably, a face of the plate to be applied to the diaphysis of the second bone fragment is transversely concave, and the cylindrical portion of the plate is truncated and has a base that is inclined to the axis of the cylindrical portion, transversely concave and longitudinally substantially convex. The plate mates thus the diaphysis face of the femur under the trochanter and distributes the progressive traction stress exerted on the end-piece and also hold axially the end-piece.

BRIEF DESCRIPTION OF THE DRAWINGS

The foregoing and other objects, features and advantages of the invention will be apparent from the following detailed description of several embodiments of the invention with reference to the corresponding accompanying drawings, in which.

DESCRIPTION OF THE PREFERRED EMBODIMENTS

In the following description of various embodiments of osteosynthesis implants in accordance with the invention, the dimensions of the various parts constituting the implants are given by way of non-limiting example. The bodies, plugs and end-pieces of the implants are made of metal, for example a titanium alloy.

Figure 1:
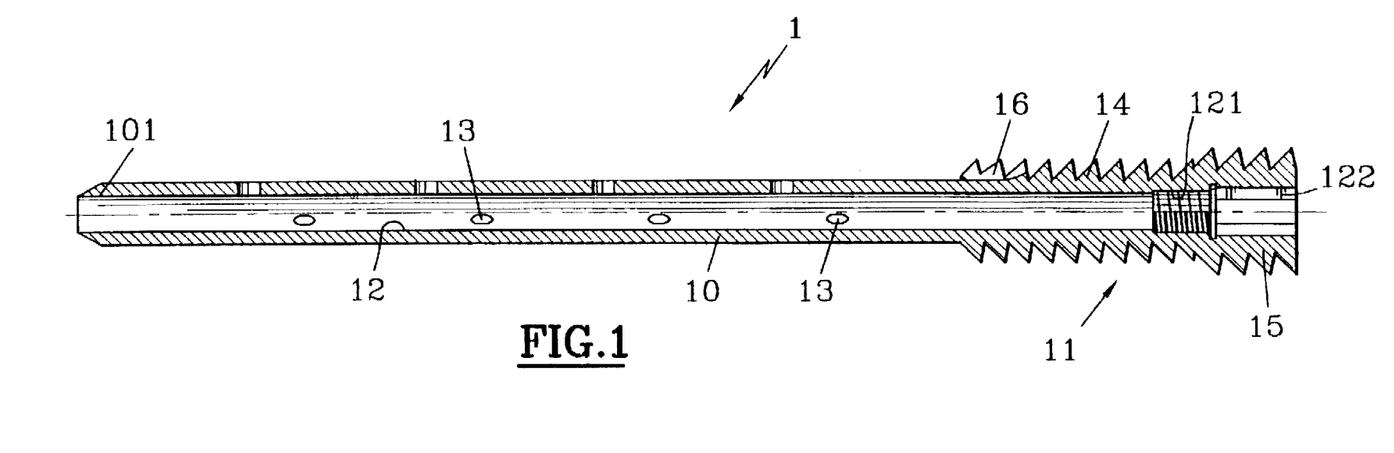
FIG. 1 is a longitudinal axial sectional view of a body of a first implant of the invention.
Figure 2:
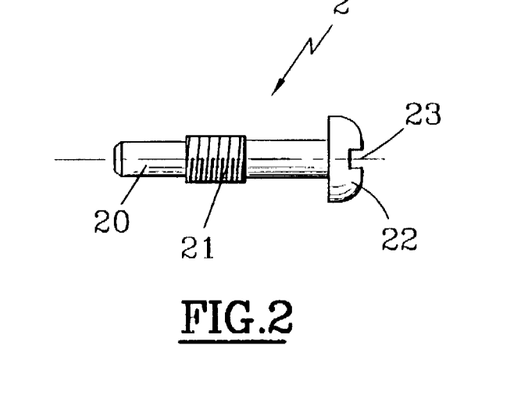
FIG. 2 is a longitudinal view of a plug of the body of the first implant.

In a first embodiment shown in FIGS. 1 and 2 an osteosynthesis implant comprises a cylindrical elongate rectilinear body 1 and a cylindrical plug 2.

The cylindrical elongate rectilinear body 1 comprises a proximal tubular vascularization portion 10 that is between 65 mm and 105 mm long, depending on the anatomy of the patient, and a distal anchor portion 11 that is 28 mm long. An internal conduit 12 having a diameter of 3 mm, except for two wider counterbores 121 and 122 at its distal end, extends along all of the length of the elongate rectilinear body 1.

The tubular portion 10 has an outside diameter of 5 mm at the time of machining the metal longitudinal rectilinear body and a final outside diameter of 5.4 mm to 5.5 mm following surface treatment. This treatment consists in depositing a first layer of T40 porous titanium 0.2 mm to 0.3 mm thick having a porosity lying between 20% and 40%. A layer of an osteogenic substance is then deposited on top of the first layer. This second layer is about 0.2 mm thick; it can be of a product that can comprise mother-of-pearl from mollusks or calcium carbonate $CaCO_3$ and lime, the calcium carbonate can be at least in part in the form of calcite and/or a smaller proportion of aragonite, and the lime can be quicklime $CaO$ and/or hydrated lime $Ca(OH)_2$. The second layer covering the body 1 is preferably deposited by thermal sputtering, using a plasma torch, of a powder compound comprising one of the following constituents: aragonite, calcite, quick lime and hydrated lime. This second layer facilitates reossification of the regeneration nucleus around the body of the implant.

The proximal end of the body terminates in a frustoconical portion 101, or by a taper, analogous to that at the end of a hypodermic needle, to facilitate penetration of the body into a hole in the bone.

The tubular portion comprises a plurality of radial orifices 13 having a diameter of 1.8 mm leading into the longitudinal internal conduit 12. These orifices are offset longitudinally and circumferentially along a helical path coaxial with the body and having a pitch of 18 mm. The radial orifices 13 are equally spaced along this helical path. In the embodiment illustrated in FIG. 1 there are three orifices 13 for each pitch of the helical path and they are equi-angularly distributed with an angular pitch of 120° and a longitudinal pitch 6 mm. The radial orifices 13 which communicate with each other through the longitudinal internal conduit 12 and the proximal end of the latter contribute to balancing the intracephalic pressure throughout the femoral head as far as the femoral trochanter after implantation of the body of the implant. The perforated tubular portion 10 constitutes a guide for revascularization by angionesis and, with the osteogenetic substance on the surface of the body, contributes to the growth of hard bone around the body 1 of the implant.

The distal anchor portion 11 is made up of two longitudinally juxtaposed sections having different exterior self-tapping screwthreads 14 and 15.

The first screwthreaded section 14 is located at the distal end of the tubular vascularization portion 10 including the orifices 13, in front of the second screwthreaded section 15. The first screwthreaded section has a nominal diameter of 8 mm, a coarse triangular pitch, known as an anti-recoil artillery pitch of 2 mm, and a screwthread root diameter of 6 mm.

The proximal end of the first screwthreaded section 14 includes three equi-angularly distributed notches 16 at 120° to each other, like the three radial orifices 13 in one pitch of the helical path previously mentioned in connection with the tubular portion 10. The notches 16 have a bottom substantially flushing with the external surface of the tubular portion 10. In a preferred embodiment, one of the walls of each notch is situated in a respective axial plane of the body 1 and the other wall of the notch is situated in the screwing direction of the screwthreads 14 and 15 at substantially 30° to 45° to the respective axial plane. The notches 16 are for starting screwthread cutting in the bone when the anchor portion 11 is inserted into a previously bored 6.5 mm diameter hole, this diameter being significantly greater than the screwthread root diameter of 6 mm, which facilitates the cutting of a screwthread in the hole by the screwthreaded section 14.

The second screwthreaded section 15 has a nominal diameter of 9 mm, an anti-recoil artillery pitch of 2.2 mm and a depth of about 2 mm. The nominal diameter and the screwthread pitch of the second screwthreaded section 15 are therefore respectively greater than the nominal diameter and the pitch of the first screwthreaded section 14. The difference in pitch between the first and second screwthreaded sections, which is equal to 0.2 mm, constitutes a means preventing an unscrewing of the body of the implant to prevent the body escaping from the epiphysis, after consolidation of the epiphysis bone around and in the threads of the anchor portion 11 of the body 1 screwed into the epiphysis bone.

As already mentioned, the distal end of the internal conduit comprises two counterbores 121 and 122.

The first counterbore 121 situated substantially at the transition between the first and second screwthreaded sections 14 and 15 is screwthreaded with a nut inside diameter of 3.3 mm and a pitch of 0.7 mm. A screwthreaded intermediate section 21 of the plug 2 screws into the first counterbore.

Figure 4:
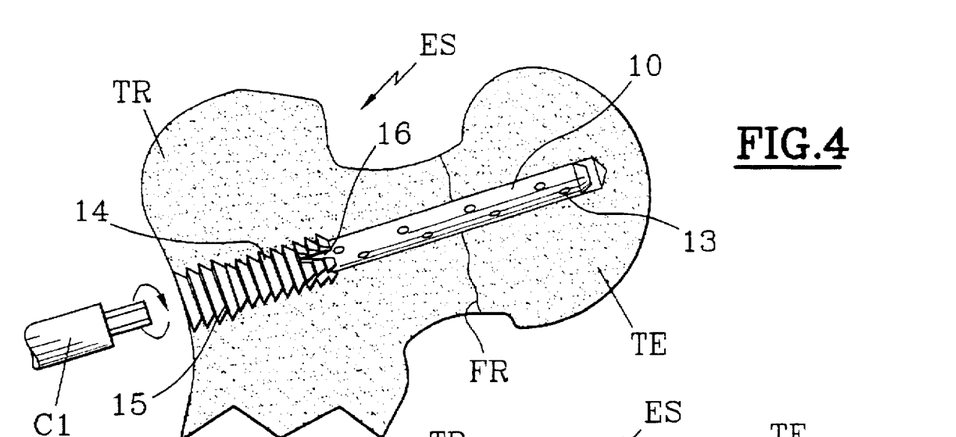
FIG. 4 is a diagrammatic sectional view in a median-lateral plane of a femur upper epiphysis showing the screwing on of the first implant.

The second counterbore 122 situated at the distal end of the body 1 and open towards the outside is in the form of a six-flats socket that circumscribes in cross-section at least the screwthreaded first counterbore 121. The flats of the second counterbore 122 are 4 mm wide and 7 mm long. The second counterbore is adapted to receive the six-flats end of a special key, as shown in FIG. 4.

Referring to FIG. 2, the plug 2 comprises a shank 20 having a length exceeding the sum of the lengths of the first and second counterbores 121 and 122 in the body 1. The shank 20 is smooth with a distal diameter of 2.8 mm, significantly less than the diameter of the internal conduit 12 of the body 1, except for an intermediate screwthreaded section 21. The intermediate screwthreaded section 21 is complementary to the first counterbore 121 so that it can be screwed into the latter. The distal end of the plug terminates in a flat head 22 with a diametral screwdriver slot 23. In a different embodiment the head of the plug is a countersunk head which is received into a countersink provided at the distal end of the body 1 of the first implant, i.e. at the distal end of the counterbore 122.

The plug 2 therefore hermetically closes off the distal end of the conduit 12 inside the body 1 of the first implant and therefore prevents any extravasation.

The first implant of the invention is implanted using the following four tools:

a drill bit 2 mm in diameter and 200 mm long, i.e., having a length greater than the body 1 of the implant which varies between about 93 mm and about 133 mm, depending on the anatomy of the patient,
  a first hollow cutting tool having an inside diameter equal to 2.1 mm so that it is guided by the bit and an outside diameter of 5.5 mm in order to bore a hole having a diameter substantially equal to the outside diameter of the tubular portion 10 of the body 1 of the first implant; the hollow cutting tool is at least as long as the bit;
  a counterboring tool made up of:
    a first guide G1 having an outside diameter of 5.2 mm and a length of 28 mm to enter the hole drilled by the first hollow cutting tool;
    a first shape milling cutter F1 having an outside diameter of 6.5 mm and a length of 22 mm to bore a first counterbore to be self-tapped by the first screwthreaded section 14; and
    a second shape milling tool F2 having an outside diameter of 7.5 mm and a length of 10 mm to bore a second counterbore to be self-tapped by the second screwthreaded section 15; and
  a first key C1 having one six-flats end complementary to the second counterbore 122 at the distal end of the body 1 of the first implant, i.e., having flats 4 mm wide and at least about 7 mm long.

Figure 3:
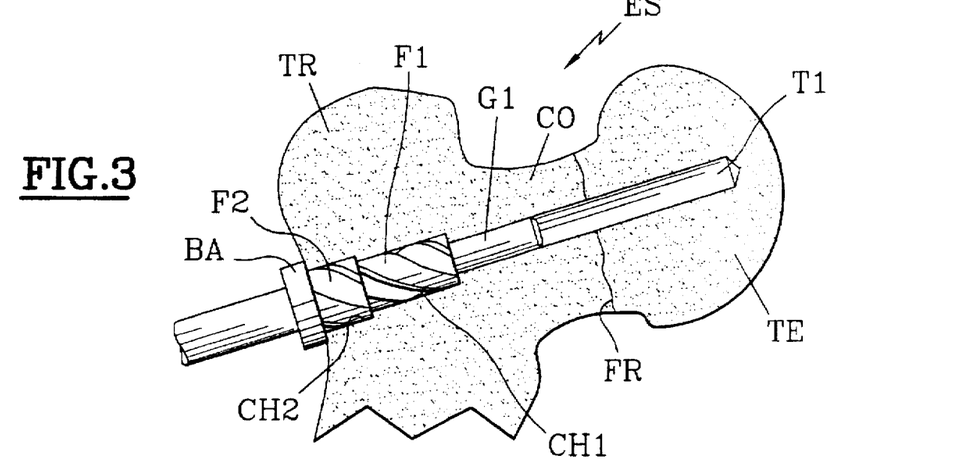
FIG. 3 is a diagrammatic sectional view in a median-lateral plane of a femur upper epiphysis in which a hole and two counterbores have been bored for implanting the first implant.
Figure 5:
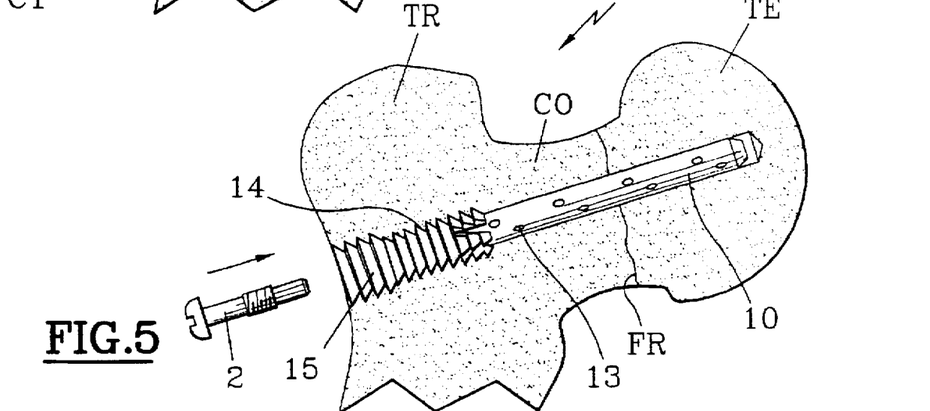
FIG. 5 is a view analogous to FIG. 4 showing the insertion of the plug into the first implant.

FIGS. 3, 4 and 5 diagrammatically illustrate various steps of machining in the upper epiphysis ES of a femur in order to implant the first implant 1 of the invention. The upper epiphysis of the femur has a necrosis resulting from a fracture FR at the level of the femoral head TE.

The drill bit is first inserted into the upper epiphysis along an axis substantially perpendicular to the line of the fracture FR and extending from the base of the femoral trochanter TR to the femoral head TE through the neck CO and therefore through the focus of the fracture. The insertion of the drill bit into the bone is in progress under the monitoring of a X-rays source. The blind hole formed in this way has a diameter of 2 mm and a depth significantly greater than the length of the first implant with the plug 2 screwed fully into the body 1.

The blind hole is widened into a 5.5 mm diameter hole T1 bored by means of the first cutting tool that fits around the first drill bit acting as a longitudinal guide. After this boring operation the first drill bit and the first cutting tool are withdrawn from the epiphysis ES.

The first and second counterbores are then milled in the trochanter TR, as shown in FIG. 3. The first milling guide G1 is threaded into the hole T1 that has just been bored in order to guide the two milling cutters. A stop ring BA with locking screw on the guide G1 limits the depth of the bores for the counterbores. The first shape milling cutter F1 widens the hole T1 in the first counterbore CH1 to a diameter of 6.5 mm, i.e., a diameter significantly greater than the screwthread root diameter of the first screwthreaded section 14 of the anchor portion 11. The length of the counterbore CH1 is substantially greater than the length of the section 14. The second shape milling cutter F2 then widens the counterbore CH1 to form the second counterbore of 7.5 mm diameter, i.e., a diameter significantly greater than the screwthread root diameter of the second screwthreaded section 15 of the anchor portion 11. The length of the second counterbore CH2 which opens onto the external face of the trochanter is substantially equal to the length of the second screwthreaded section 15 at the distal end of the implant body 1.

After removing the counterboring tool, the implant body 1 is placed in the femoral upper epiphysis ES, as shown in FIG. 4. The tubular portion 10 is driven into the long blind hole T1 using an impactor until the notched proximal end 16 of the first screwthreaded section 14 of the anchor portion 11 is flush with the external face of the trochanter. The six-flats end of the key C1 is inserted into the six-flats counterbore 122 of the implant body 1. Pressure is applied to the key C1 to engage the distal end of the first screwthreaded section 14 into the shoulder between the two counterbores CH1 and CH2 formed in the trochanter. The key C1 is then used as a screwdriver in order to screw the implant body 1 into the bone until the first and second screwthreaded sections 14 and 15 of the implant body 1 are entirely housed within the respective counterbores CH1 and CH2 made in the bone. As this screwing proceeds the screwthreaded sections 14 and 15 cut themselves a screwthread in the counterbores CH1 and CH2.

In this way the implant is finally implanted into the femoral upper epiphysis ES. Because of the difference in the pitches and because of the difference in the diameters of the screwthreaded sections 14 and 15, the body 1 cannot become unscrewed and move in the distal direction towards the external face of the epiphysis after bone forms around the body. The orifices 13 and the internal conduit 12 communicate on either side of the fracture FR, in the neck CO and the head TE, and bring about revascularization, i.e., irrigation between bone fragments eliminated by the fracture.

The key C1 is withdrawn. As shown in FIG. 5, the plug 2 is finally screwed into the screwthreaded counterbore 121 of the body 1 until the head 23 presses against the distal end face of the body and so blocks off the distal end of the internal conduit 12 of the implant body 1 which thereby becomes a blind bored conduit open only at the proximal end.

Figure 6:
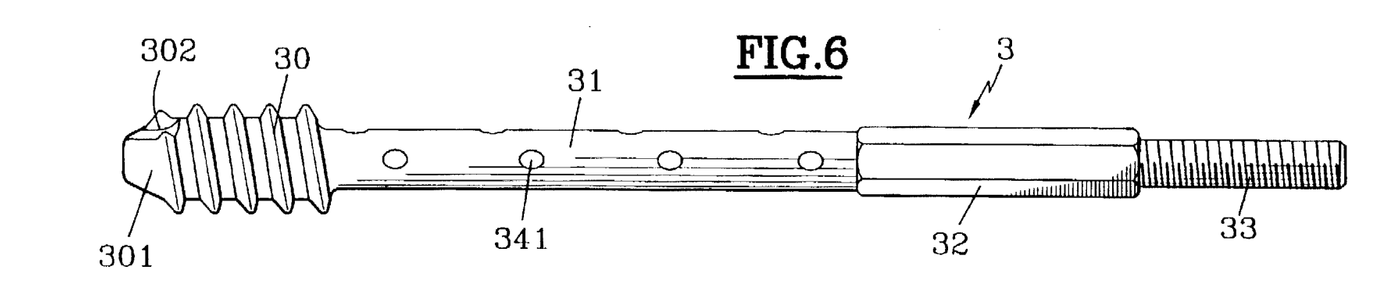
FIG. 6 is a longitudinal view of a body of a second implant of the invention.
Figure 7:
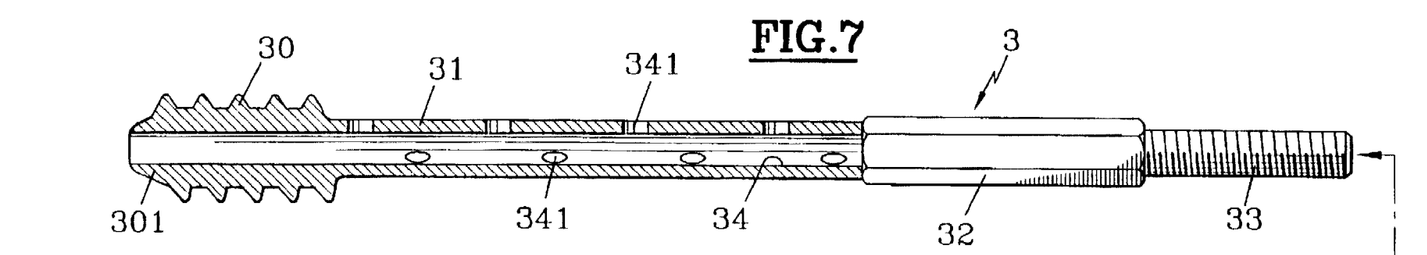
FIG. 7 is an exploded view in longitudinal axial section of the second implant.

Referring now to FIGS. 6 and 7, a second osteosynthesis implant comprises an elongate rectilinear body 3 of generally cylindrical shape, like a stud bolt, a cylindrical distal end-piece with a double external screwthread 4, a helical spring 5 and a screwthreaded hollow plug 6.

The elongate rectilinear body 3 comprises from its proximal end towards its distal end, a proximal self-tapping screwthreaded tubular portion 30, a perforated smooth tubular portion 31, a hexagonal cross-section operating portion 32 and finally a screwthreaded distal portion 33.

A blind internal revascularization conduit 34 with a proximal mouth 3 mm in diameter is provided in the proximal portion 30 and the smooth portion 31. As in the first embodiment, plural radial orifices 341 1.8 mm in diameter are formed in the smooth tubular portion 31. These orifices are disposed along a helical path coaxial with the body 3 and regularly distributed in the longitudinal direction with an angular pitch of 120°. The orifices 341 communicate with each other via the longitudinal internal conduit 34 and with the mouth at the proximal end of the internal conduit, the latter being blind at the distal end at the level of the operating portion 32, as shown in FIG. 7.

As in the body of the first implant, the smooth tubular portion 31 has an outside diameter of 5.4 mm to 5.5 mm after thermal deposition on the surface of a porous titanium first layer and a second layer of a mother-of-pearl product or of a product including calcium carbonate in the form of calcite and/or aragonite and quick lime and/or hydrated lime. The smooth tubular portion 31 is made in different sizes between 20 mm and 60 mm in order to suit the anatomy of the patient.

The proximal portion 30 of the body 3 of the second implant designed to be implanted in the femoral head TE has an external screwthread over a length of 15 mm with a nominal diameter of 8 mm and a screwthread root diameter of 6 mm. This screwthread has a pitch of 3 mm with a particular self-tapping profile known as a spongy or soft bone screwthread profile. The self-tapping portion 30 has a proximal end 301 of frustoconical shape including two diametrally opposite notches 302 extending longitudinally as far as the start of the self-tapping screwthread. The notches 302 can be similar to the notches 16. The frustoconical end 301 with the notches 302 starts the cutting of a self-tapping screwthread in the bone.

The operating portion 32 and the screwthreaded portion 33 at the distal end of the body 3 are respectively 25 mm and 10 mm long.

As shown in FIG. 7, the distal end-piece 4 comprises an internal conduit made up of first, second and third sections having progressively larger cross-sections from the proximal end towards the distal end of the end-piece.

The first section 40 constitutes the proximal section of the internal conduit in the end-piece 4 and has a six-flats cross-section complementary to the hexagonal cross-section of the operating section 32 of the body 3. However, the 10 mm length of the end-piece section 40 is less than the 25 mm length of the hexagonal cross-section portion 32 of the body 3. The body portion 32 can therefore slide in the end-piece section 40 in the axial direction when the end-piece 4 is being fixed into the femoral trochanter TR to pull in the distal direction the body 3 anchored in the femoral head TE by the proximal self-tapping portion 30, as explained below. The polygonal cross-section sliding coupling between the portion 32 and the section 40 also enables screwing of the proximal self-tapping portion 30 of the body 3 together with screwthreaded portions on the periphery of the end-piece 4, as explained below.

The section 41 in the end-piece 4 is a smooth cylindrical section situated between the proximal and distal sections 40 and 42. It is 12 mm long. The 6.5 mm diameter of the smooth section 41 is greater than the greatest width of the hexagonal cross-section of the proximal section 40 but less than the greatest width of the hexagonal cross-section of the distal section 42 of the end-piece. The helical spring 5, the length of which when unstressed is 12 mm, and at least part of the plug 6, which have respective outside diameters of 6.3 mm and 6.4 mm, are completely housed within the intermediate end-piece section 41. The proximal end 51 of the spring 5 is pressed against an internal shoulder 43 between the sections 40 and 41 by the thrust exerted by the plug 6 pressed against the distal end 52 of the spring 5. The body portion 32 can pass through the spring 5 if necessary.

The turns of the spring 5 are covered with a synthetic plastic material, such as polyurethane, to form a sheath 53 around the turns which slows the expansion of the spring after it is compressed between the shoulder 43 and the plug 6. The synthetic plastic material sheath 53 around the turns of the spring also contributes to attenuation of microdisplacements and vibrations to which the second implant may be subjected after implantation.

The third section 42 of the end-piece 4 has a hexagonal cross-section and is located at its distal end. It has flats 4 mm wide and 8 mm long in order to receive the six-flats end of the previously mentioned key C1. When the proximal section 40 of the end-piece 4 is threaded over the operating portion 32 of the body 3, the distal screwthreaded portion 33 of the body passes freely through the other two sections 41 and 42 of the internal conduit in the end-piece 4. To push the spring 5 into its housing 41, the plug 6 is screwed onto the distal screwthreaded body portion 33 which has a nominal diameter of 4 mm and a fine pitch of 0.6 mm.

As also shown in FIG. 7, the periphery of the end-piece 4 has a first screwthreaded anchor section 44 at its proximal end and a second screwthreaded anchor section 45 at its distal end, in a similar way to the first and second screwthreaded sections 14 and 15 constituting the anchor portion 11 of the body 1 of the first implant.

The first screwthreaded section 44 has a nominal diameter of 11 mm, a screwthread root diameter of 9 mm and an anti-recoil artillery pitch of 3 mm identical to the pitch of the proximal body portion 30, and extends over a length of 20 mm, as far as the smooth cylindrical section 41 of the internal conduit. The proximal end of the first self-tapping section 44 includes three distributed notches 46 that are equally spaced in the axial direction with an angular spacing of 120° to start the cutting of a screwthread by means of the first section 44, in a similar manner to the notches 16 at the proximal end of the anchor portion 11 of the body 1 of the first implant.

The second screwthreaded section 45 has an outside diameter of 13 mm and an anti-recoil artillery pitch of 3.2 mm and extends over a length of 10 mm. The proximal end of the section 45 also includes three notches 47 equiangularly distributed at 120° to start the cutting of a screwthread by means of the second section 45. The notches 47 can be offset in the radial direction relative to the notches 46, for example by about 60°.

The difference in pitch, 3.2−3=0.2 mm, between the two screwthreaded sections 44 and 45 prevents unscrewing of the end-piece 4.

The screwthreaded plug 6 has a length that is less than the sum of the lengths of the smooth intermediate section 41 and the hexagonal cross-section section 42 inside the end-piece, and that is less than the length of the distal screwthreaded portion 33 of the body 3 so that the plug 6 is guided in the smooth section 41 and can be moved a few millimeters in the axial direction inside the end-piece 4 by the compressed spring 5. The 6.4 mm outside diameter plug 6 has a slot 61 at its distal end by means of which its screwthreaded bore 62 is screwed onto the distal screwthreaded portion 33 of the body 3 so that its proximal face 63 pushes the spring 5 against the shoulder 43 of the proximal section 40 and the smooth intermediate section 41 inside the end-piece. The plug 6 therefore has two functions, to close the internal conduit in the end-piece at the distal end and to compress the damper spring 5.

The second implant is implanted using the following tools:

the 2 mm diameter first drill bit, having a length greater than that of the body 3 of the second implant, which can vary between 70 mm and 110 mm depending on the anatomy of the patient;

a second hollow cutting tool having an inside diameter equal to 2.1 mm so that it can be guided by the first drill bit and an outside diameter of 6 mm in order to bore a hole having a diameter substantially equal to the smallest screwthread root diameter of the threads on the second implant, which in this example is that of the proximal screwthreaded portion 30 of the body 3; the second hollow cutting tool is at least as long as the first drill bit;

a second counterboring tool comprising:
  a second guide having an outside diameter of 5.7 mm and a length of 28 mm to enter the hole bored by the second hollow cutting tool;
  a third shape milling tool having an outside diameter of 9.5 mm and a length of 22 mm to bore a first counterbore to be self-tapped by the proximal end-piece section 44; and
  a fourth shape milling tool having an outside diameter of 11 mm and a length of 10 mm to bore a second counterbore to be self-tapped by the distal end-piece section 45;

the first special key C1 having a six-flats end complementary to the distal counterbore 42 of the end-piece, i.e., having flats 4 mm wide and a length of at least 8 mm;

a second special key having a cylindrical end hole with a blind screwthread, which is similar to the plug 6, to be screwed onto the distal screwthreaded portion 33 of the body 3 and enters the internal end-piece sections 41 and 42 so as to pull the body 3, and especially the femoral head TE into which the proximal portion 30 is screwed, in the direction of the trochanter TR;

tweezers for fitting the spring 5; and a screwdriver for screwing the plug 6 onto the screwthreaded body section 33 to compress the spring 5.

Figure 8:
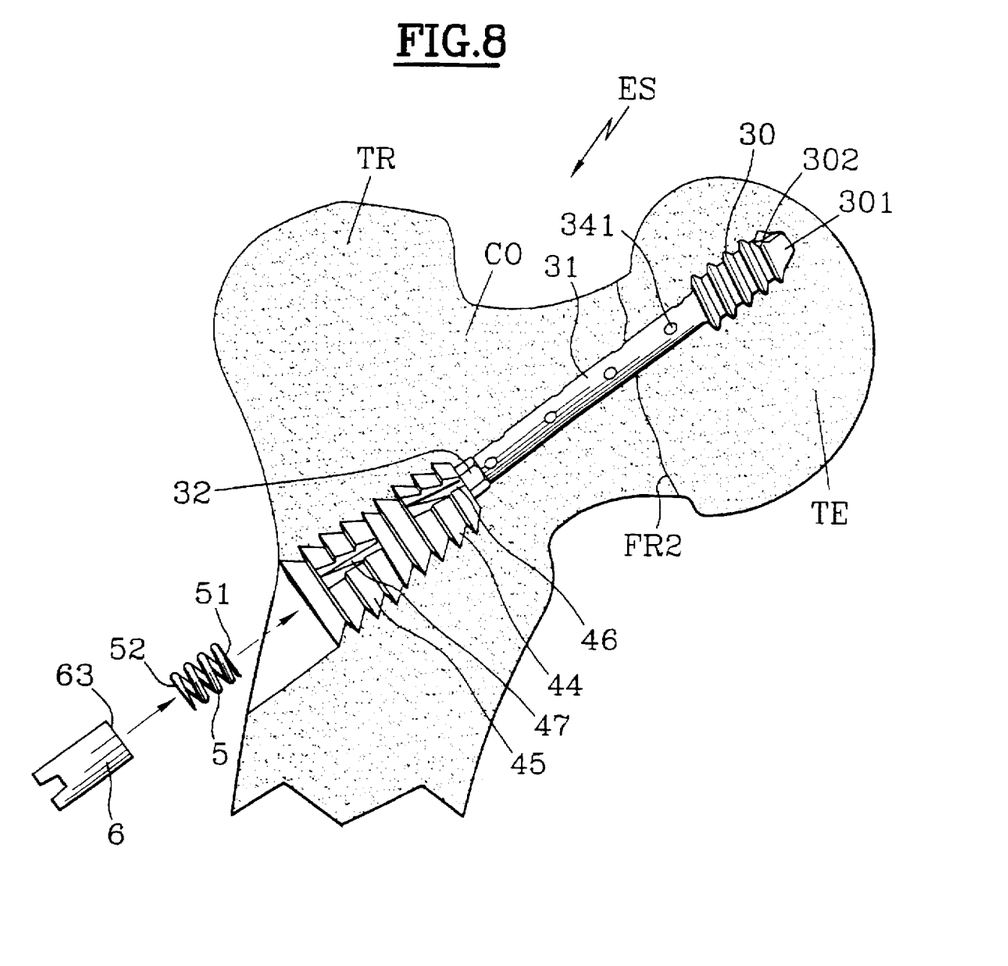
FIG. 8 is a diagrammatic sectional view in a median-lateral plane of a femur upper epiphysis showing the insertion of a spring and a plug into the body of the second implant already inserted into the epiphysis.

In reference to FIG. 8, the various stages of boring into the upper epiphysis ES of the femur to implant the second implant of the invention are shown. They are substantially the same as those shown in FIGS. 3 through 5. The second implant is more particularly suited to fractures FR2 of the neck of the femur sub-capital, trans-cervical or even basicervical, with varying Powles angle.

As with the first implant, the first drill bit is introduced into the upper epiphysis ES of the femur, through the trochanter TR, then the neck CO of the femur and finally part of the femoral head TE in order to form a blind hole substantially perpendicular to the fracture FR2. The depth and the direction of this hole are monitored by X-rays so that the length bored in this way is at least equal to the overall length of the second implant.

The second hollow cutting tool is then threaded over the drill bit as far as the end of the latter to increase the diameter of the blind hole to 6 mm, which is substantially equal to the screwthread root diameter of the proximal self-tapping portion 30 of the body 3 of the second implant. The second hollow cutting tool and the first drill bit are then withdrawn from the epiphysis ES.

Two counterbores are then formed using the second counterboring tool. The second milling cutter guide is inserted into the 6 mm bone hole drilled previously and provides a guide for the third and fourth shape milling cutters. The third shape milling cutter bores a first counterbore 9.5 mm in diameter to a substantially greater depth equal to the length of the proximal self-tapping section 44 of the end-piece, whilst the fourth shape milling cutter bores a second, wider counterbore with a diameter of 11 mm to a depth substantially greater than the length of the distal self-tapping section 45 of the end-piece. The depth of the counterbores are determined by a stop ring similar to the ring BA which abuts against the external face of the trochanter when the counterbore is completed. The two milling cutter diameters of 9.5 mm and 11 mm are respectively substantially equal to the screwthread root diameters of the proximal and distal self-tapping sections 44 and 45 of the end-piece.

When the counterboring tools have been withdrawn, the body 3 of the second implant with the end-piece 4 threaded over the hexagonal cross-section portion 32 is placed in the two-counterbores blind hole in the bone formed in this way through the fracture FR2 in the upper femoral epiphysis ES as shown in FIG. 8. The proximal notches 302 and the proximal self-tapping portion 30 of the body 3 bite into the bone and cut a screwthread in the bone from the internal shoulder between the 6 mm diameter long hole and the 9.5 mm diameter first counterbore. The proximal self-tapping portion 30 continues to move forward into the blind hole in the bone. Just before reaching the bottom of this hole, a first axial pressure is applied so that the proximal screwthreaded section 44 of the end-piece cuts a screwthread in the first counterbore, this section 44 having the same pitch as the body portion 30. A second substantially higher pressure is then applied so that the distal screwthreaded section 45 of the end-piece cuts a screwthread with a greater pitch in the second counterbore. The screwthread cutting operations are effected using the hexagonal-end key C1 which cooperates with the internal distal section 42 of the end-piece, the proximal internal section 40 of which is engaged around the hexagonal cross-section portion 32 of the body 3.

With the self-tapping body portion 30 installed at the bottom of the hole in the femoral head TE and the end-piece 4 immobilized in the trochanter TR in this way, the second key is screwed onto the distal body portion 33. Traction is applied in the distal direction, longitudinally of the body of the second implant, by means of the second key so as to pull the femoral head TE fragment against the trochanter TR and thus close up the fracture.

After withdrawal of the second key the spring 5 is picked up with the tweezers and inserted into the smooth intermediate section 41 inside the end-piece, bearing on the shoulder 43.

The plug 6 is screwed by means of a screwdriver onto the distal body portion 33 of the body 3 so that it compresses the spring 5. The spring 5 therefore constitutes damper means adapted to push the end-piece 4 in the proximal direction and the body 3 in the distal direction, and procures compression at the fracture FR2, i.e., permanent and progressive traction of the femoral head TE in which the body 3 is anchored by the self-tapping portion 30 against the trochanter TR in which the end-piece 4 is anchored by the self-tapping sections 44 and 45, unscrewing being impossible. This compression stabilizes the fracture to favor faster consolidation of the fracture.

Pseudo-arthrosis of a sub-capital transcervical fracture of the neck of the femur, even with an oblique Powles angle, can be treated using the second implant of the invention. Because the latent expansion of the spring 51 pushes the end-piece in the proximal direction and the body 3 in the distal direction, the second implant procures dynamic compression of the focus of the pseudo-arthrosis.

Figure 9:
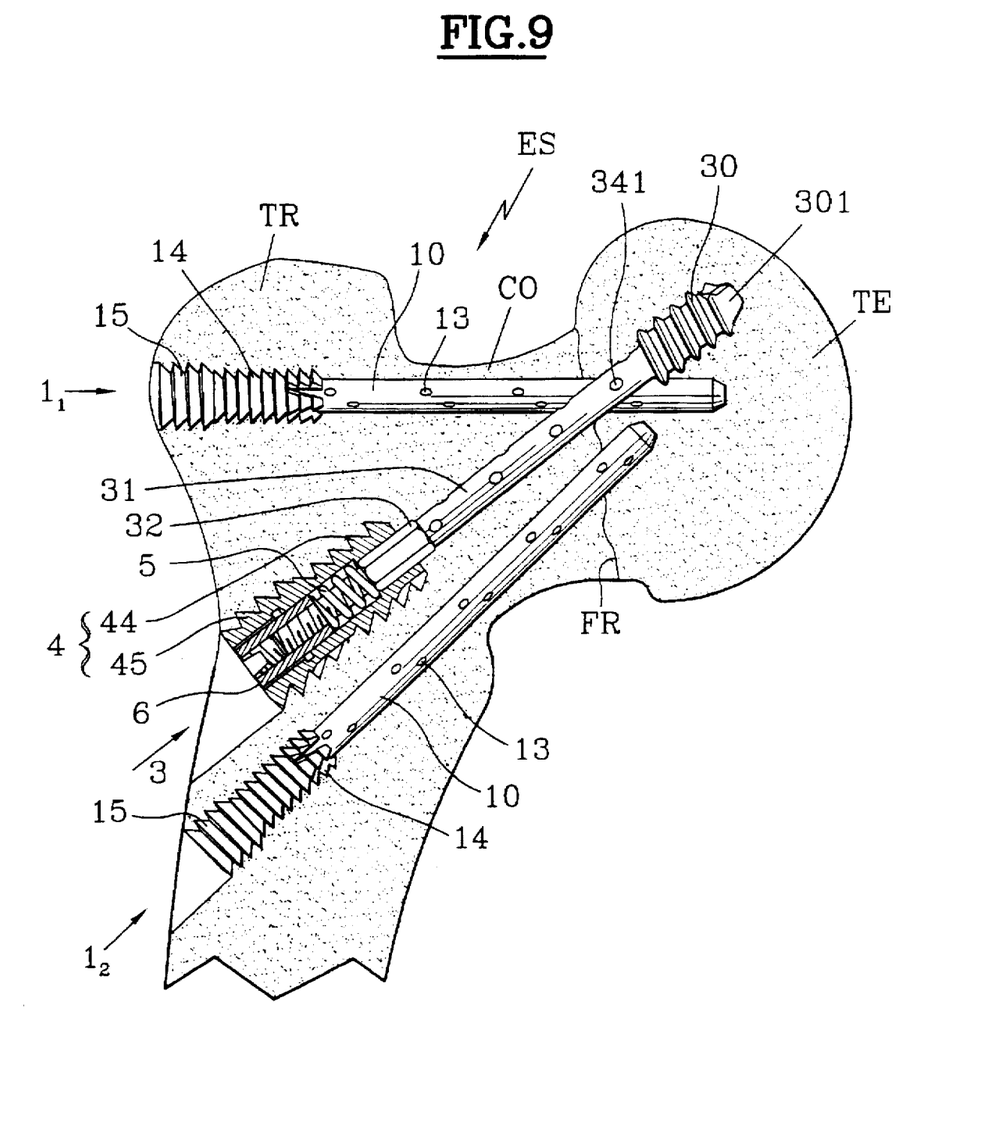
FIG. 9 is a diagrammatic sectional view in a median-lateral plane of a femur upper end in which two first implants and one second implant have been implanted.

This compression can be complemented by using at least one first implant of the invention. Referring to FIG. 9, two first implants $1_1$ and $1_2$ are disposed above and under the previous second implant 3 substantially in the same plane, as perpendicular as possible to the plane PS of the pseudo-arthrosis.

The pseudo-arthrosis can be treated without using pedicular grafting and without ostetomy because of the dynamic compression of the pseudo-arthrosis associated with the bone generating features of the implants, the angiogenic capability of the tubular portions 13 and 31 and the osteogenic covering on their external surfaces.

With this type of indication, a triangular arrangement enables immediate post-surgery load bearing. This arrangement is achieved by fitting a second implant of the invention to procure axial dynamic compression in the femoral neck CO associated with two first implants of the invention, one of which is oblique from bottom to top and the other of which is substantially horizontal and extends from front to rear.

Figures 10, 11:
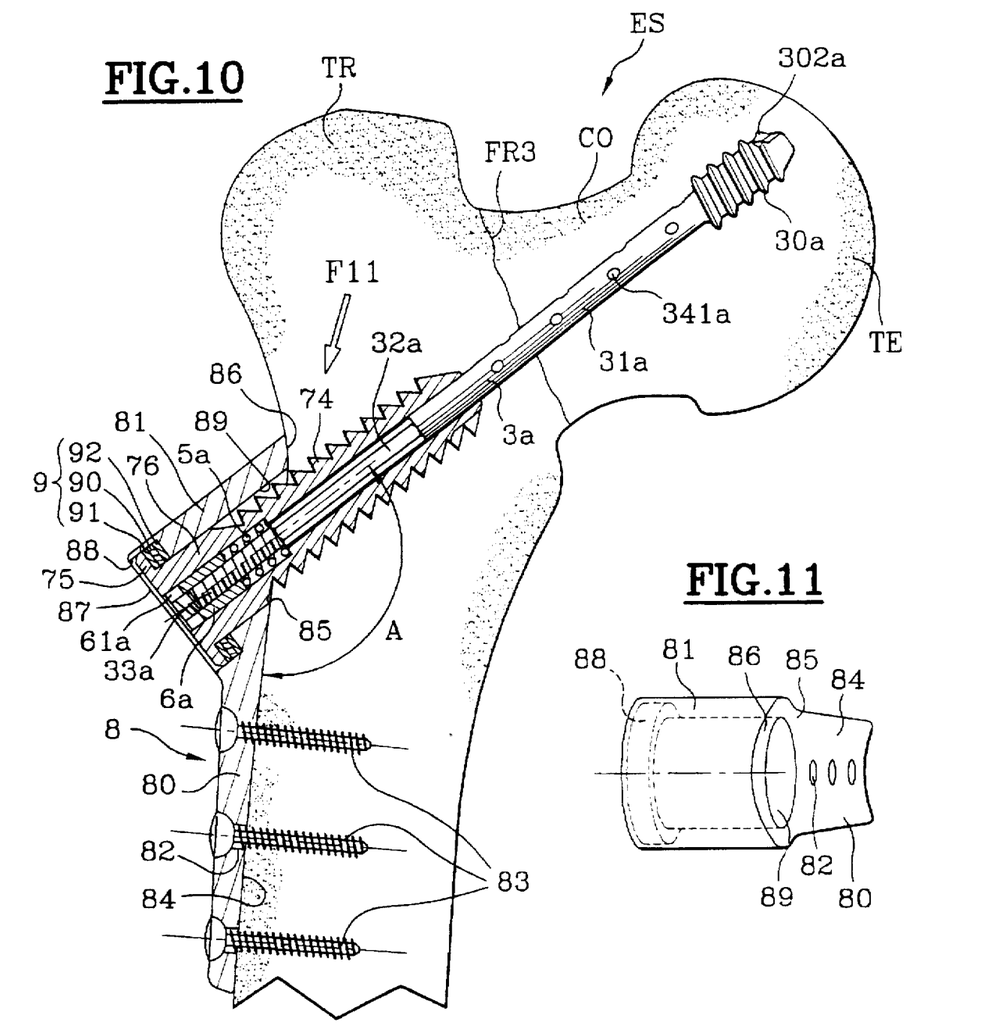
FIG. 10 is a diagrammatic sectional view in a median-lateral plane of a femur upper epiphysis in which a third implant of the invention with a diaphysis plate is implanted.
FIG. 11 is a view of the diaphysis plate as seen in the direction of the arrow F11 in FIG. 10.
Figure 12:
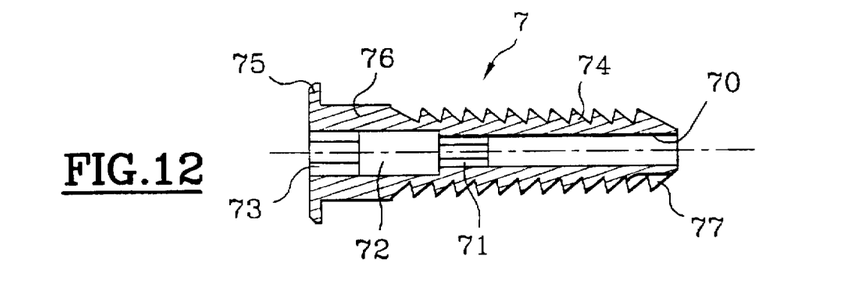
FIG. 12 is a view in axial section of an end-piece of the third implant.

A third osteosynthesis implant of the invention is shown in FIGS. 10, 11 and 12 and comprises an elongate rectilinear body 3a of generally stud bolt-like cylindrical shape, a cylindrical distal end-piece 7 with a base and an external screwthread, containing a helical spring 5a and a screwthreaded hollow plug 6a, and a diaphysis plate 8.

The longitudinal rectilinear body 3a is similar to the elongate rectilinear body 3 of the second implant shown in FIGS. 6 and 7, but is longer than the latter so that its screwthreaded distal portion 33a projects from the external face of the epiphysis. Thus the body 3a comprises from its proximal end towards its distal end, a proximal self-tapping screwthreaded tubular portion 30a, a perforated smooth tubular portion 31a, a hexagonal cross-section operating portion 32a and finally a screwthreaded distal portion 33a. A blind internal revascularization conduit with a proximal mouth and plural radial orifices 341a in the smooth tubular portion 31a, as in the first and second implants of the invention, is formed in the proximal portion 30a and the smooth portion 31a.

As in the body of the first implant, the smooth tubular portion 31a has an outside diameter of 5.4 mm to 5.5 mm after thermal deposition.

As shown in FIG. 12, the distal end-piece 7 comprises an internal conduit made up of first, second, third and fourth sections 70 through 73 having progressively larger transverse cross-sections from the proximal end towards the distal end of the end-piece.

The first section 70 is the longest and constitutes the proximal section of the internal conduit in the end-piece 4. The section 70 is cylindrical with a circular cross-section substantially larger than the greatest width of the hexagonal cross-section of the operating portion 32a of the body 3a.

The second section 71 has a six-flats cross-section complementary to the hexagonal cross-section of the operating portion 32a of the body 3a and extends over a length less than the length of the operating portion 32a of the body 3a so that the body portion 32a can slide axially in the end-piece section 71 when the end-piece 7 is fixed into the femoral trochanter TR to pull the body 3a anchored into the femoral head TE by the proximal self-tapping portion 30a in the distal direction. As in the second implant, the polygonal cross-section sliding coupling between the body portion 32a and the section 71 also enables screwing of the proximal self-tapping portion 30a of the body 3a together with a screwthreaded portion on the periphery of the end-piece 7, in the bone.

The sections 71, 72 and 73 in the end-piece 7 have similar functions to those of the sections 40, 41 and 42 in the end-piece 4.

The section 72 is a smooth cylindrical section between the sections 71 and 73. The diameter of the smooth section 72 is greater than the greatest width of the hexagonal cross-section of the section 71 in the end-piece but substantially equal to the smallest width of the hexagonal cross-section of the distal section 73. All of the helical spring 5a and at least part of the plug 6a are housed in the intermediate end-piece section 72. The proximal end of the spring 5a is pressed against an internal shoulder between the sections 71 and 72 by the thrust exerted by the plug 6a applied against the distal end of the spring 5a. The spring 5a is preferably coated with a plastics material like the spring 5.

The third section 73 of the end-piece 7 has a hexagonal cross-section and is located at the distal end of the end-piece to receive the six-flats end of the previously mentioned key C1. When the section 71 of the end-piece 7 is threaded over the operating section 32a of the body 3a, the distal screwthreaded section 33a of the body 3a passes freely through the two internal conduit sections 72 and 73 of the end-piece. To push the spring 5a into its housing 72, the plug 6a is screwed onto the distal screwthreaded body portion 33a.

The screwthreaded plug 6a is similar to the plug 6 and can be moved a few millimeters in the axial direction in the end-piece 7 by the compressed spring 5a, being guided in the smooth section 72. The plug 6a has a slot 61a at its distal end so that it can be screwed around the distal screwthreaded portion 33a of the body 3a to compress the spring 5a between the proximal face of the spring 5a and the shoulder between the proximal section 72 and the smooth intermediate section 71 inside the end-piece 7.

As also shown in FIG. 12, the periphery of the end-piece 7 has a long proximal self-tapping screwthreaded anchor section 74 extending three-quarters the length of the end-piece and similar to the second screwthreaded section 45 and consequently having a diameter and/or a pitch different from those of the anchor portion 30a of the body 3a. The screwthreaded anchor section 74 has a surface treatment similar to that of the body 1.

The end-piece 7 also has at the periphery a distal thin circular base 75 and a smooth cylindrical section 76 situated between the base and the anchor section 74. The diameter of the smooth section 76 is greater than the outer diameter of the anchor section 74. The base 75 and the section 76, which are not included in the second implant, cooperate with the diaphysis plate 8.

The diaphysis plate 8 comprises, in the lower part, an elongate rectilinear lower anchor portion 80 to be implanted along an external face of the diaphysis of the femur and, in the upper part, an upper guide bearing portion 81.

Three holes 82 are formed in the anchor portion 80. The holes 42 extend substantially perpendicular to the faces of the portion 80 and are longitudinally aligned on the latter to receive anchor screws 83 with clearance.

As seen in FIG. 11, the diaphysis face 84 of the anchor portion has a concave cross-section to mate with the convex cross-section of the femoral diaphysis.

The guide and bearing portion 81 is a truncated cylindrical shank oblique to the longitudinal axis of the anchor portion 80. The axis of the shank 81 towards the trochanter TR is at an angle A of about 120° to 140° to the anchor portion 80. The proximal inclined base 85 of the shank 81 is also transversely concave, extending the diaphysis face 84, and has a convex longitudinal end 86 that substantially follows the concave curved profile in a median-lateral plane of the femoral epiphysis, at the base of the trochanter TR. The cylindrical shank 81 has a spot facing 88 of an axial smooth bore 89 in the inside of a distal base 87 perpendicular to the shank axis. The spot facing 88 and the bore 89 receive the thin base 75 and the distal cylindrical section 76 of the end-piece 7, respectively, which slide in them. The axial length of the spot facing 88 and of the bore 89, i.e., the shortest distance between the bases 87 and 85 of the shank 81 situated at the same end as the anchor portion 80, is substantially greater than the axial length of the base 75 and of the section 76 so that the latter are completely housed within the shank 81.

In the spot facing 88 there are provided means 9 for damping micro-displacement between the end-piece 7 anchored under the trochanter TR and the diaphysis plate 8. The damping means 9 attenuates any lever effect between the plate 8 and the combination of the body 3a and end-piece 7 due to microslipping of bone fragments at the focus of the fracture FR3. The damping means 9 comprises at least one washer 90 made from a damping material, such as an elastomer or polyurethane or silicone rubber, threaded over the smooth section 76. In the embodiment shown in FIG. 10 the washer 90 is sandwiched between two metal washers 91 and 92 that are preferably bonded by heat to the washer 90; this assembly of washers 90, 91 and 92 is threaded over the section 76 and clamped to the distal base of the section 76, in the spot facing 88, between the distal thin base 75 of the end-piece 7 and the bottom of the spot facing 88. In a different embodiment, the washer assembly includes only a damping material washer 90 and a single metal washer 91 or 92.

The third implant is preferentially used for sub-trochanter fractures FR3. It is implanted in the following manner.

The femoral plate 8 is fixed to the diaphysis face of the femur, locating the guide and bearing portion 81 on the sub-trochanter bend. The three anchor screws 83 are screwed into the femur through the plate holes 82, if necessary into pilot holes previously bored in the femur, up to clamp the plate 8 against the femoral diaphysis.

A cylindrical guide having an inside diameter substantially equal to that of a drill bit is slid into the bore 89.

The drill bit, longer than the body 3a, is introduced into the upper epiphysis ES of the femur, for example by rotating it by hand, through the aforementioned cylindrical guide, the trochanter TR, the fracture FR3, the neck CO of the femur and finally part of the femoral head TE to form a blind hole substantially perpendicular to the fracture FR3. The depth and the direction of this hole are monitored by X-rays so that the length bored in this phase is substantially equal to the length of the portions 30a, 31a and 32a of the body 3a.

After removing the previously mentioned cylindrical guide, a hollow cutting tool is then threaded over the first drill bit as far as the end of the latter to enlarge the blind hole to a diameter that is substantially equal to the screwthread root diameter of the proximal self-tapping portion 30a of the body 3a of the third implant. The above mentioned drill bit and the second cutting tool are then withdrawn from the epiphysis ES.

A cylindrical milling guide is inserted into the long hole just bored in the bone, and guides a shape milling cutter to bore a counterbore having a diameter equal to the screwthread root diameter of the self-tapping section 74 of the end-piece, to a depth substantially equal to the length of the section 74. The depth of the counterbore is determined by a stop ring, similar to the ring BA (FIG. 3), which abuts against the external base 87 of the plate shank 81 when the end of the counterbore is reached. This counterbore may not be necessary if the diameter of the end-piece section 74 is substantially equal to that of the body portion 30a.

When the counterboring tools have been withdrawn, the body 3a of the third implant with the end-piece 7 threaded over the hexagonal cross-section portion 32a and with the assembly of washers 90, 91 and 92 threaded over the smooth end-piece section 76 is placed in the counterbored blind hole in the bone formed in this way through the fracture FR3 in the femoral upper epiphysis ES, as shown in FIG. 10. Proximal notches 302a and the self-tapping screwthread of the proximal portion 30a of the body 3a bite into the bone and cut a screwthread into the bone from the bottom of the counterbore. A proximal self-tapping portion 30a continues to move forward into the blind hole in the bone. Just before the portion 30a reaches the bottom of this hole, a first axial pressure is applied so that proximal notches 77 and the screwthread of the self-tapping section 74 of the end-piece 7 bite into and cut a screwthread into the counterbore in the bone. The section 74 can have the same screwthread pitch as the body portion 30a or preferably a larger pitch. The screwthread cutting operations are carried out using the hexagonal end key C1 which cooperates with the internal distal section 73 of the end-piece 7 the internal hexagonal cross-section portion 71 of which is engaged around the hexagonal cross-section portion 32a of the body 3a.

With the self-tapping body section 30a installed at the bottom of the hole in the bone in the femoral head TE and the end-piece 7 immobilized in the trochanter TR by the screwthreaded section 74 in this way, a second special key, similar to the blind screwthread key already used for the second implant, is screwed onto the distal body portion 33a. Traction is applied by means of the second key in the distal direction, longitudinally of the body 3a, to pull the femoral head TE fragment against the trochanter TR and thus to close up the fracture FR3.

After withdrawal of the second key, the spring 5a is picked up with the tweezers and inserted into the smooth section 72 inside the end-piece, bearing against the shoulder between the sections 72 and 71.

The plug 6a is screwed by means of a screwdriver onto the distal body portion 33a of the body 3a to compress the spring 5a. This compression procures permanent and progressive traction of the femoral head TE in which the body 3a is anchored by the self-tapping portion 30a against the trochanter TR in which the end-piece 7 is anchored by the self-tapping section 74, with unscrewing impossible, at the level of the fracture FR3 and in particular in the trochanter and sub-trochanter regions. The compression is distributed along the femoral diaphysis by application of the plate anchor portion 80 against the diaphysis, this distribution being notably effective when the forces applied in a subtrochanter fracture FR3 are high. Relative to the seating of the implant on the diaphysis, the lever effect due to lateral microdisplacements and vibrations are attenuated by the retention of the distal end 76 of the end-piece 7 in the upper shank 81 and the damping washer means 9 accommodated in the shank spot facing 88. The body 3a of the implant is held axially, preventing intra-cephalic movement. The distribution of compression combined with the attenuation of microdisplacements enhances rapid consolidation of the fracture.

What we claim is:

1. An implant for osteosynthesis of a fracture between first bone fragment and a second bone fragment, comprising:
   (a) an elongate implant body having a proximal end and a distal end, said implant body containing a longitudinal conduit extending from an opening in said proximal end toward said distal end, said body also containing a plurality of longitudinally spaced through openings extending radially outwardly from said conduit, said body proximal end being adapted for insertion within alined bores formed in the first and second bone fragments on opposite sides of the fracture; and
   (b) first self-tapping means arranged at one end of said body for connecting said body one end with the associated bone fragment.

2. Arm implant as claimed in claim 1, comprising a plug located in said distal end of said body and obstructing said longitudinal conduit.

3. The implant as claimed in claim 2 wherein said distal end of said longitudinal conduit comprises a screwthread into which a screwthreaded shank of said plug is screwed.

4. The implant as claimed in claim 1 wherein said distal end of said conduit comprises a counterbore opening to the exterior of said body and having a polygonal cross-section to receive a complementary cross-section end of a key for screwing said body into a hole in said first bone fragment and second bone fragment.

5. The implant as claimed in claim 1 wherein said self-tapping portion is located at said distal end of said body to be implanted in said second bone fragment.

6. The implant as claimed in claim 5 wherein said self-tapping portion comprises two screwthreaded sections having different screwthreads.

7. The implant as claimed in claim 5 wherein said self-tapping portion includes at least one distal longitudinal notch for starting screwthread cutting.

8. The implant as claimed in claim 1 wherein said self-tapping portion comprises a proximal screwthreaded section and a distal screwthreaded section, said distal screwthreaded section having at least one of pitch and nominal diameter respectively greater than the respective one of pitch and nominal diameter of said proximal screwthreaded section.

9. The implant as claimed in claim 1 wherein said self-tapping portion is located at the proximal end of said body to be installed in said first bone fragment.

10. The implant as claimed in claim 9 wherein said self-tapping portion includes at least one distal longitudinal notch for starting screwthread cutting.

11. Implant means as defined in claim 1, wherein said first self-tapping means is arranged at said proximal end of said implant body; and further including:
   (c) a tubular end-piece concentrically mounted for sliding movement on an intermediate portion of said implant body between the ends thereof;
   (d) second self-tapping means mounted on said end-piece for connecting said end piece with the other of the bone fragments; and
   (e) damping means connected with the other end of said implant body for biasing said end piece toward said proximal end of said implant body.

12. Implant means as defined in claim 11, and further including:
   (f) a diaphysis plate containing a through opening in which said end-piece is mounted, said end piece having an external flange portion that limits the extent of travel of said end-piece toward the implant body proximal end; and
   (g) means for securing said diaphysis plate to the second bone fragment.

* * * * *